United States Patent

Kayahara et al.

[11] Patent Number: 5,888,827
[45] Date of Patent: *Mar. 30, 1999

[54] METHOD FOR DETERMINATION OF CHOLESTEROL IN LOW-DENSITY LIPOPROTEIN OR VERY LOW-DENSITY LIPOPROTEIN

[75] Inventors: Norihiko Kayahara, Kawasaki; Toshio Tatano, Numazu; Eiko Shutoh, Ohita; Hiroyuki Sugiuchi, Kumamoto; Tetsumi Irie, Kumamoto; Kaneto Uekama, Kumamoto, all of Japan

[73] Assignee: Kyowa Medex Co., Ltd., Tokyo, Japan

[ * ] Notice: The term of this patent shall not extend beyond the expiration date of Pat. No. 5,736,406.

[21] Appl. No.: 737,738
[22] PCT Filed: May 15, 1996
[86] PCT No.: PCT/JP96/00665
  § 371 Date: Nov. 19, 1996
  § 102(e) Date: Nov. 19, 1996
[87] PCT Pub. No.: WO96/29599
  PCT Pub. Date: Sep. 26, 1996

[30] Foreign Application Priority Data
Mar. 20, 1995  [JP]  Japan ................................... 7-060993

[51] Int. Cl.⁶ .................................................. G01N 33/92
[52] U.S. Cl. .............................. 436/71; 436/13; 436/166; 435/11; 435/19; 435/28; 422/61; 252/408.1
[58] Field of Search ................................ 436/13, 71, 73, 436/79, 91, 95, 164, 166, 174, 904; 435/11, 14, 19, 28; 422/61; 252/408.1

[56] References Cited

U.S. PATENT DOCUMENTS

| 4,544,630 | 10/1985 | Ziegenhorn et al. | 435/11 |
| 4,626,511 | 12/1986 | Artiss et al. | 436/8 |
| 4,647,532 | 3/1987 | Watanabe et al. | 435/28 |
| 4,678,598 | 7/1987 | Ogino et al. | 510/102 |
| 4,778,753 | 10/1988 | Yamanishi et al. | 435/10 |
| 4,851,335 | 7/1989 | Kerscher et al. | 435/11 |
| 4,892,815 | 1/1990 | Kerscher et al. | 436/71 X |
| 5,032,503 | 7/1991 | Khanna et al. | 435/7.6 |
| 5,691,159 | 11/1997 | Miyauchi et al. | 435/11 |
| 5,736,406 | 4/1998 | Miyauchi et al. | 436/71 |

FOREIGN PATENT DOCUMENTS

| 0676642 | 10/1995 | European Pat. Off. . |
| 0698791 | 2/1996 | European Pat. Off. . |
| 0699767 | 3/1996 | European Pat. Off. . |

OTHER PUBLICATIONS

Sjoblom et al., Lipids, vol. 24, No. 6 (1989) 532–34.

Akai et al., Osaka City Medical Journal, vol. 25, No. 1 (1979) 25–36.

*Primary Examiner*—Maureen M. Wallenhorst
*Attorney, Agent, or Firm*—Fitzpatrick, Cella, Harper & Scinto

[57] ABSTRACT

Cholesterol in low-density lipoprotein (LDL) or very low-density lipoprotein (VLVL) in a sample is determined in the presence of a sugar compound and/or a protein-solubilizing agent.

29 Claims, No Drawings

METHOD FOR DETERMINATION OF CHOLESTEROL IN LOW-DENSITY LIPOPROTEIN OR VERY LOW-DENSITY LIPOPROTEIN

TECHNICAL FIELD

The present invention relates to a method for the determination of cholesterol in low-density lipoprotein (LDL) or very low-density lipoprotein (VLDL) (hereinafter referred to as LDL cholesterol or VLDL cholesterol) which is important with respect to lipid metabolism in the field of clinical diagnosis.

BACKGROUND ART

LDL is considered to have the function to supply cholesterol to peripheral cells and to be a direct factor in occurrence of various types of arteriosclerosis such as coronary arteriosclerosis. It is known that LDL level in blood is useful as an indicator of arteriosclerosis. The relationship between VLDL which is rich in triglycerides (TG) and arteriosclerosis has also been noted. Currently, the determination of LDL cholesterol is carried out by the ultracentrifugation method, the electrophoretic method, the conversion method, etc., and that of VLDL cholesterol is carried out by the ultracentrifugation method, the electrophoretic method, etc. In the ultracentrifugation method, which is employed as a basic method, LDL or VLDL is separated by the difference in specific gravity using an ultracentrifuge for separation, and the amount of cholesterol therein is determined [Adv. Lipid Res., 6, 1 (1968)]. However, this method is defective in accuracy, simplicity, economic efficiency, etc. In the electrophoretic method, LDL or VLDL is separated by using a cellulose acetate membrane or agarose gel as a support, and the amount of cholesterol therein is enzymatically determined [Clinical Test (Rinsho Kensa), 29, 1344 (1985)]. This method is defective in simplicity, economic efficiency, etc. In the conversion method, the amount of LDL cholesterol is calculated according to the following equation [Clin. Chem.,18, 499 (1972)].

(Amount of LDL cholesterol)=(Amount of total cholesterol)–(Amount of HDL cholesterol)–(Amount of triglycerides)/5

However, the use of this method is restricted by the serum TG content, the type of hyperlipemia, etc., and so this method is defective in simplicity, accuracy, applicability to the analysis of a large number of samples, etc. As described above, conventional methods for the determination of LDL cholesterol or VLDL cholesterol are not suitable for the analysis of a large number of samples, the rapid analysis, and the analysis with an autoanalyzer which is widely used in the field of clinical testing. Further, in these methods, manual errors are liable to occur, for example, when the amount of the LDL fraction separated is determined using a measuring pipette. However, if a blood serum sample is directly added to a reagent containing cholesterol esterase and cholesterol oxidase without fractionation of LDL or VLDL, the resultant test system is not different from a system for the determination of total cholesterol, and LDL cholesterol or VLDL cholesterol cannot be specifically determined.

DISCLOSURE OF THE INVENTION

The present inventors have determined the amount of cholesterol in high-density lipoprotein (HDL), LDL, VLDL, and chylomicron (CM), each of which had been fractionated through ultracentrifugation, using a reagent for the determination of cholesterol containing a sugar compound and/or a protein solubilizing agent, and found that these lipoproteins differ in reactivity to the reagent based on the combinations of the sugar compound and/or the protein solubilizing agent, which leads to the difference in the reactivity of cholesterol in HDL, LDL cholesterol, VLDL cholesterol, and cholesterol in CM. This finding has led to the completion of the present invention.

The present invention relates to a method for the determination of LDL cholesterol or VLDL cholesterol in a sample, which comprises determining the amount of LDL cholesterol or VLDL cholesterol in the sample in the presence of a sugar compound and/or a protein solubilizing agent. In this method, a divalent metal salt may be added to the determination system in order to improve the specificity.

The present invention also provides a reagent for the determination of cholesterol in LDL or VLDL, which contains a sugar compound and/or a protein solubilizing agent; and a reagent for the determination of cholesterol in LDL or VLDL, which is a kit composed of a sugar compound and a protein solubilizing agent.

As the sugar compound, glucose derivatives are preferably used. Examples of the glucose derivative include compounds represented by general formula (I):

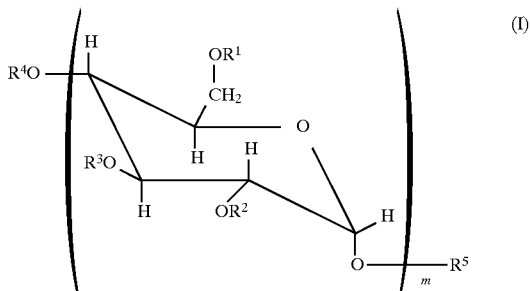

wherein $R^1$, $R^2$, and $R^3$ independently represent hydrogen, substituted or unsubstituted alkyl, substituted or unsubstituted alkanoyl, $SO_3M^2$ (in which $M^2$ is hydrogen or a metal), -(glucosyl)$_p$—H (in which p is 1 or 2), or -(maltosyl)$_q$—H (in which q is 1 or 2); $R^4$ and $R^5$ independently represent hydrogen, a metal, or $SO_3M^3$ (in which $M^3$ is hydrogen or a metal); and m is an integer of 6 to 8; and compounds represented by general formula (II):

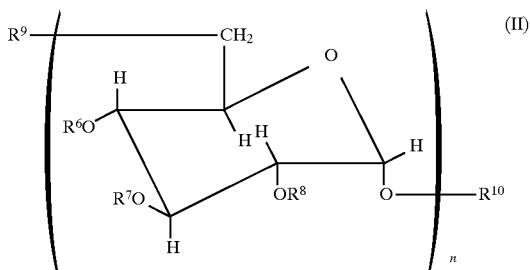

wherein $R^6$, $R^7$, and $R^8$ independently represent hydrogen or $SO_3M^4$ (in which $M^4$ is hydrogen or a metal); $R^9$ represents hydrogen, $OM^5$ (in which $M^5$ is hydrogen or a metal), or $OSO_3M^6$ (in which $M^6$ is hydrogen or a metal); $R^{10}$ represents hydrogen, a metal, or $SO_3M^7$ (in which $M^7$ is hydrogen or a metal); and n is an integer of 4 to 8000.

Preferable examples of the protein solubilizing agents are compounds represented by general formula (III):

$$R^{11}(C_2H_4O)_a\text{---}(C_3H_6O)_bR^{12} \qquad (III)$$

wherein each a and b represents an integer of 0 to 200; $R^{11}$ represents $R^{20}$—X—O— (in which $R^{20}$ is alkyl or alkenyl, and X is a single bond or CO) or H—(CH$_2$CH$_2$O)$_c$—N(R$^{21}$)— (in which c is an integer of 1 to 200, and R$^{21}$ is alkyl or alkenyl); and R$^{12}$ represents C$_2$H$_4$COOR$^{22}$, C$_3$H$_6$COOR$^{23}$, C$_2$H$_4$CH(COOR$^{24}$)$_2$, or C$_2$H$_4$CH(COOR$^{25}$)(COOR$^{26}$) (in which R$^{22}$, R$^{23}$, R$^{24}$, R$^{25}$, and R$^{26}$ independently represent hydrogen, a metal, alkyl, or alkenyl), provided that at least one of a and b is not 0, and the two elements may be located at random; compounds represented by general formula (IV):

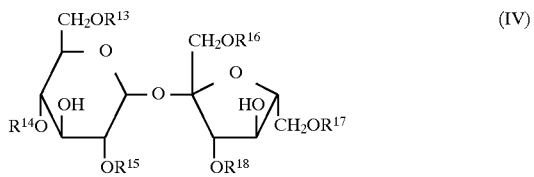

(IV)

wherein R$^{13}$, R$^{14}$, R$^{15}$, R$^{16}$, R$^{17}$, and R$^{18}$ independently represent alkanoyl; and compounds represented by general formula (V);

(V)

wherein R$^{19}$ represents alkyl, alkenyl, or substituted or unsubstituted aryl; Y represents a single bond,

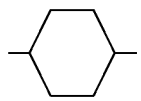

—O—, —CH(R$^{27}$)— (in which R$^{27}$ is alkyl or alkenyl), —CH$_2$CH(OH) (CH$_2$)$_d$— (in which d is an integer of 1 to 22), —CH=CH(CH$_2$)$_e$— (in which e is an integer of 1 to 22), —OCOCH(CH$_2$COOR$^{28}$)— (in which R$^{28}$ is alkyl or alkenyl), or a mixture thereof; and M$^1$ represents hydrogen or a metal.

The compounds represented by general formulae (I) to (V) are hereinafter referred to as Compounds (I) to (V), respectively.

In the definitions of the groups in formulae (I) to (V), the alkyl and the alkyl moiety of the alkanoyl mean a straight-chain or branched alkyl group having 1 to 22 carbon atoms such as methyl, ethyl, propyl, isopropyl, butyl, isobutyl, sec-butyl, tert-butyl, pentyl, isopentyl, neopentyl, hexyl, heptyl, decyl, pentadecyl, icosanyl and docosanyl. The alkenyl means a straight-chain or branched alkenyl group having 2 to 22 carbon atoms such as vinyl, propenyl, butenyl, pentenyl, hexenyl, heptenyl, decenyl, pentadecenyl, icosenyl and docosenyl. The aryl means phenyl or naphthyl. The metal includes lithium, sodium, and potassium.

Examples of the substituents of the substituted alkyl and the substituted alkanoyl are hydroxy, carboxy, and sulfo. An example of the substituent of the substituted aryl is alkyl, and the alkyl has the same meaning as defined above.

As the sugar compound, cyclodextrin derivatives are preferable among Compounds (I) and (II), and methylated cyclodextrin is especially preferable. Examples of the preferred compounds are α-cyclodextrin, β-cyclodextrin, γ-cyclodextrin, dimethyl-β-cyclodextrin, trimethyl-β-cyclodextrin, hydroxyethyl-β-cyclodextrin, 2-hydroxypropyl-α-cyclodextrin, 2-hydroxypropyl-β-cyclodextrin, carboxymethyl-β-cyclodextrin, glucosyl-β-cyclodextrin, maltosyl-α-cyclodextrin, maltosyl-β-cyclodextrin, partially-methyl-β-cyclodextrin, α-cyclodextrin sulfate, and β-cyclodextrin sulfate.

As the protein solubilizing agent, nonionic surfactants and anionic surfactants are especially preferable among the surfactants such as Compounds (III), (IV), and (V). Examples of the nonionic surfactants are polyoxyethylene lauryl ether, polyoxyethylene cetyl ether, polyoxyethylene stearyl ether, polyoxyethylene oleyl ether, polyoxyethylene behenyl ether, polyoxyethylene monolaurate, polyoxyethylene monostearate, polyoxyethylene monooleate, polyoxyethylene laurylamine, polyoxyethylene stearylamine, and sucrose fatty acid ester. Examples of the anionic surfactants are sodium dodecylbenzenesulfonate, sodium n-dodecylbenzenesulfonate, sodium lauryl sulfate, and higher alcohol sulfuric acid ester sodium salt.

As the divalent metal salt, 0.01–20 mM magnesium salt, calcium salt, manganese salt, nickel salt, or cobalt salt is used. Preferably, 0.01–20 mM magnesium salt is used.

The present invention is characterized by the presence of the sugar compound and/or the protein solubilizing agent in the reagent system for the determination of cholesterol. The system for the determination of cholesterol follows a general method based on the following reaction principle, provided that the chromogen and the measurement wavelength are not limited to those shown below.

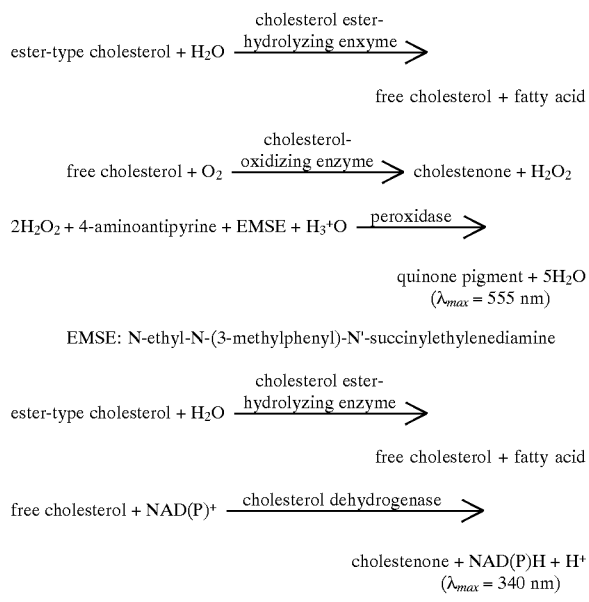

As the chromogen, combinations of 4-aminoantipyrine and Trinder's reagent [General Catalog of Dojin Kagaku Kenkyusho, 19th ed. (1994)] can be used, as well as generally employed combinations of 4-aminoantipyrine and phenols such as phenol, 4-chlorophenol, m-cresol and 3-hydroxy-2,4,6-triiodobenzoic acid (HTIB). Examples of the Trinder's reagents are anilines such as N-sulfopropylaniline, N-ethyl-N-(2-hydroxy-3-sulfopropyl)-m-toluidine (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-sulfopropyl-m-toluidine (TOPS), N-(2-hydroxy-3-sulfopropyl)-3,5-dimethoxyaniline (HDAOS), N,N-dimethyl-m-toluidine, N,N-disulfopropyl-3,5-dimethoxyaniline, N-ethyl-N-sulfopropyl-m-anisidine, N-ethyl-N-sulfopropylaniline, N-ethyl-N-sulfopropyl-3,5-dimethoxyaniline, N-sulfopropyl-3,5-dimethoxyaniline, N-ethyl-N-sulfopropyl-3,5-dimethylaniline, N-ethyl-N-(2-hydroxy-3-sulfopropyl)-m-anisidine, N-ethyl-N-(2-hydroxy-3-sulfopropyl)aniline and N-ethyl-N-(2-hydroxy-3-sulfopropyl)-3,5-dimethoxyaniline, N-ethyl-N-(3-methylphenyl)-N'-succinylethylenediamine (EMSE), and N-ethyl-N-(3-methylphenyl)-N'-acetylethylenediamine. As the chromogen of high sensitivity, 10-(N-methylcarbamoyl)-3, 7-bis(dimethylamino)phenothiadine (MCDP) disclosed in Japanese Published Examined Patent Application No. 33479/85, bis[3-bis(4-chlorophenyl)methyl-4-dimethylaminophenyl]amine (BCMA) disclosed in Japanese Published Examined Patent Application No. 27839/92, the chromogens disclosed in Japanese Published Unexamined Patent Application No; 296/87, etc. can be used. These chromogens of high sensitivity may be used in combination with 4-aminoantipyrine or with the Trinder's reagents enumerated above. The concentration of the chromogen is preferably 0.01–10 mg/ml, and is limited by the solubility.

As the cholesterol ester-hydrolyzing enzyme, cholesterol-oxidizing enzyme and cholesterol dehydrogenase, commercially available enzymes can be used. For example, cholesterol esterase and lipoprotein lipase derived from microorganisms or animals having the ability to hydrolyze cholesterol ester, cholesterol oxidase derived from microorganisms having the ability to oxidize cholesterol to form hydrogen peroxide, and cholesterol dehydrogenase derived from microorganisms or animals may be used. In order to improve the specificity and stability of these enzymes, they may be chemically modified with a group having polyethylene glycol as a main component, a water-soluble oligosaccharide residue, or a sulfopropyl group. Further, enzymes which are obtained by introduction of genes of the enzymes mentioned above into other microorganisms and subsequent expression thereof, optionally followed by chemical modification, and enzymes which are obtained by modification of genes of the enzymes mentioned above and subsequent expression thereof, optionally followed by chemical modification, can also be used.

Examples of the reagent for modifying the enzymes (chemical modifier) are compounds wherein polyethylene glycol and a group which can be bonded to an amino group are connected [e.g. Sunbright VFM4101 (NOF Corporation) wherein polyethylene glycol and a group which can be bonded to an amino group such as N-hydroxysuccinimido group are connected], Sunbright AKM series, ADM series, and ACM series [NOF Corporation: Chemical Engineering Monographs (Kagaku Kogaku Ronbunshu), 20 (3), 459 (1994)], which are compounds having the polyalkylene glycol structure and the acid anhydride structure, compounds wherein a copolymer of polyethylene glycol and polypropylene glycol and a group which can be bonded to an amino group are connected, copolymers of polyethylene glycol monomethacryl monomethyl ether and maleic anhydride, etc. Further, polyurethane P4000 activated (Boehringer Mannheim, Directions for Enzyme Modification Set) which is a chemical modifier for polyurethane, Dextran T40, TCT-activated (same as above) which is a chemical modifier for dextran, 1,3-propanesultone, etc. are also usable.

A method for the reaction of an enzyme with a chemical modifier is described below. It should be noted, however, that the reaction is not limited to this method. First, the enzyme is dissolved in a buffer such as phosphate buffer of pH 8 or above, and then, for example, Sunbright (0.01–500 times molar quantity of the enzyme) is added to the solution at 0°–50° C., followed by stirring for 5 minutes to 24 hours. The resulting reaction mixture is used as it is, or it is used after removal of low molecular weight compounds by ultrafiltration, if necessary. The cholesterol ester-hydrolyzing enzyme, cholesterol-oxidizing enzyme, and cholesterol dehydrogenase are advantageously used at a concentration of 0.1–100 u/ml.

The method of the present invention can be applied to body fluid samples containing LDL or VLDL such as blood and urine.

Representative procedures for the determination according to the present invention are described below.

Procedure 1

In conducting the method of the present invention, a solution of the sugar compound and/or a solution of the protein solubilizing agent are first prepared. The solution of the sugar compound is prepared by dissolving the sugar compound in a suitable buffer, for example, 50 mM Tris-HCl buffer (pH 7.4) such that the concentration of the sugar compound becomes, for example, 100 mM or less, preferably 3 to 80 mM at the time of the reaction. The sugar compound may be initially added to the reagent for the determination of cholesterol. The solution of the protein solubilizing agent is prepared by dissolving the protein solubilizing agent in a suitable buffer, for example, 50 mM Tris-HCl buffer (pH 7.4) and is added to the reagent for the determination of cholesterol such that the concentration of the protein solubilizing agent becomes, for example, 50 g/l or less, preferably 0.1 to 20 g/l at the time of the reaction. The reagent of the present invention is prepared from the solution of the sugar compound and/or the solution of the protein solubilizing agent containing the reagent for the determination of cholesterol (when the solution of the protein solubilizing agent is not used, the sugar compound is initially added to the reagent for the determination of cholesterol), and maintained at 20° to 50° C., preferably 30° to 40° C. for approximately 5 minutes. Then, the sample as such or the sample which has been diluted with water or physiological saline is added to the above-mentioned reagent, and the reaction is conducted for 5 to 30 minutes. After the completion of reaction, the absorbance of the reaction mixture is measured at 340 to 900 nm, for example, at 555 nm in the case of measurement at a single wavelength, and at 600 nm (main wavelength) and 700 nm (sub-wavelength) in the case of measurement at two wavelengths, to calculate the amount of cholesterol (in the case of measurement at two wavelengths, the amount of cholesterol is calculated from the difference between the absorbances at two wavelengths).

The amount of cholesterol in each of the HDL, LDL, VLDL, and CM fractions obtained by fractionation of a serum by ultracentrifugation was determined by using the above-described reagent. As a result, it was confirmed that HDL cholesterol, LDL cholesterol VLDL cholesterol, and CM cholesterol differ in reactivity to the reagent based on the combinations of the sugar compound and the protein solubilizing agent, and that these lipoproteins differ in reactivity to the reagent based on the combinations of the sugar compound and the protein solubilizing agent.

The difference among the lipoproteins in reactivity to a reagent for the determination of cholesterol (unmodified) containing a combination of 5 mM sugar compound and 5 g/l polyoxyethylene monolaurate, which is a protein solubilizing agent, is shown in Table 1.

TABLE 1

| Sugar compound | HDL | LDL | VLDL | CM |
| --- | --- | --- | --- | --- |
| α-Cyclodextrin | + | ++ | + | + |
| β-Cyclodextrin | + | ++ | + | + |
| γ-Cyclodextrin | + | ++ | + | ++ |

TABLE 1-continued

| Sugar compound | HDL | LDL | VLDL | CM |
|---|---|---|---|---|
| Dimethyl-β-cyclodextrin | − | +++ | +++ | +++ |
| Trimethyl-β-cyclodextrin | − | +++ | + | + |
| Hydroxyethyl-β-cyclodextrin | − | ++ | + | + |
| 2-Hydroxypropyl-α-cyclodextrin | + | ++ | ++ | ++ |
| 2-Hydroxypropyl-β-cyclodextrin | − | ++ |  | ++ |
| Carboxymethyl-β-cyclodextrin | + | ++ | ++ | ++ |
| Glucosyl-β-cyclodextrin | + | ++ | ++ | ++ |
| Maltosyl-α-cyclodextrin | + | ++ | ++ | ++ |
| Maltosyl-β-cyclodextrin | + | ++ | + | + |
| Partially-methyl-β-cyclodextrin | + | ++ | + | + |
| α-Cyclodextrin sulfate | + | ++ | + | + |
| β-Cyclodextrin sulfate | + | ++ | + | + |

−, +, ++, and +++ indicate the degree of reaction,
and the order of reactivity is − < + < ++ < +++.

The difference among the lipoproteins in reactivity to a reagent for the determination of cholesterol (unmodified) containing a combination of 5 mM trimethyl-β-cyclodextrin, which is a sugar compound, and 5 g/l protein solubilizing agent is shown in Table 2.

TABLE 2

| Protein solubilizing agent | HDL | LDL | VLDL | CM |
|---|---|---|---|---|
| Polyoxyethylene lauryl ether | − | +++ | +++ | +++ |
| Polyoxyethylene cetyl ether | + | ++ | + | + |
| Polyoxyethylene stearyl ether | + | ++ | + | + |
| Polyoxyethylene oleyl ether | + | ++ | + | + |
| Polyoxyethylene behenyl ether | + | ++ | + | + |
| Polyoxyethylene monolaurate | − | +++ | + | + |
| Polyoxyethylene monostearate | − | ++ | + | + |
| Polyoxyethylene monooleate | − | ++ | + | + |
| Polyoxyethylene laurylamine | − | ++ | + | + |
| Polyoxyethylene stearylamine | − | ++ | + | + |
| Sucrose fatty acid ester | + | ++ | ++ | + |
| Sodium dodecylbenzenesulfonate | − | ++ | + | + |
| Sodium n-dodecylbenzenesulfonate | − | ++ | ++ | ++ |
| Sodium lauryl sulfate | − | ++ | ++ | ++ |
| Higher alcohol sulfuric acid ester sodium salt | + | ++ | + | + |

−, +, ++, and +++ indicate the degree of reaction,
and the order of reactivity is − < + < ++ < +++.

Procedure 2

A solution of the sugar compound is prepared by dissolving the sugar compound in a suitable buffer, for example, 50 mM Tris-HCl buffer (pH 7.4) such that the concentration of the sugar compound becomes, for example, 100 mM or less, preferably 3 to 80 mM at the time of the reaction. A solution of the protein solubilizing agent is prepared by dissolving the protein solubilizing agent in a suitable buffer, for example, 50 mM Tris-HCl buffer (pH 7.4) such that the concentration of the protein solubilizing agent becomes, for example, 50 g/l or less, preferably 0.1 to 20 g/l at the time of the reaction. To the solution of the sugar compound and/or the solution of the protein solubilizing agent heated in advance at 20° to 50° C., preferably 30° to 40° C., for example, at 37° C., is added the sample as such or the sample which has been diluted with water or physiological saline.

After the mixture is heated, for example, at 37° C. for 5 minutes, the absorbance of the mixture is measured at 555 nm (E1). Subsequently, the reagent for the determination of cholesterol heated in advance at 20° to 50° C., preferably 30° to 40° C., for example, at 37° C., is added to the mixture, followed by stirring. After 5 minutes, the absorbance of the mixture is measured at the same wavelength [E2 (value after the adjustment based on the concentration)]. The amount of cholesterol is calculated by separately subjecting a standard solution of cholesterol at a known concentration to the same procedure and comparing the respective values of (E2−E1).

Certain embodiments of the present invention are illustrated in the following examples.

Best Mode for Carrying Out the Invention

EXAMPLE 1

Determination of LDL cholesterol was carried out by the method of the present invention in which the amount of LDL cholesterol was directly determined and by the agarose electrophoretic method [Clinical Test (Rinsho Kensa), 29, 1344 (1985)] for comparison.

Composition of Reagents in the Method of the Present Invention:

| First reagent | |
|---|---|
| Trimethyl-β-cyclodextrin | 5 mM |
| Polyoxyethylene monolaurate | 5 g/l |
| EMSE | 1.1 mM |
| Tris buffer (pH 7.0) | 30 mM |
| Second reagent | |
| Cholesterol esterase (unmodified) | 1.0 U/ml |
| Cholesterol oxidase (unmodified) | 5.0 U/ml |
| Peroxidase | 25 U/ml |
| 4-Aminoantipyrine | 2.2 mM |
| Tris buffer (pH 7.0) | 30 mM |

In the method of the present invention, 50 μl of a blood serum sample was added to 2.25 ml of the first reagent heated in advance at 37° C. The mixture was heated at 37° C. for 5 minutes, and then the absorbance of the mixture was measured at 555 nm (E1). Subsequently, 0.75 ml of the second reagent heated in advance at 37° C. was added to the mixture, followed by stirring. After 5 minutes, the absorbance of the mixture was measured at the same wavelength [E2 (value after the adjustment based on the concentration)]. The amount of LDL cholesterol was calculated by separately subjecting a standard solution of cholesterol at a concentration of 200 mg/dl to the same procedure and comparing the respective values of (E2−E1).

In the agarose electrophoretic method, after the electrophoresis, cholesterol in the lipoprotein fraction on the support was enzymatically stained, and the amount of LDL cholesterol was determined by densitometry (Cliniscan 2; Helena Institute).

The results are shown in Table 3.

TABLE 3

| Sample | Concentration of LDL cholesterol (mg/dl) | |
|---|---|---|
| | Method of the present invention | Electrophoretic method |
| 1 | 62 | 55 |
| 2 | 85 | 81 |
| 3 | 77 | 72 |
| 4 | 148 | 138 |
| 5 | 122 | 116 |
| 6 | 156 | 151 |
| 7 | 150 | 139 |
| 8 | 133 | 121 |
| 9 | 133 | 123 |
| 10 | 140 | 129 |

As shown in Table 3, the results obtained by the method of the present invention closely correlated with the results obtained by the electrophoretic method.

EXAMPLE 2

Determination of LDL cholesterol was carried out by the same procedure as in the method of the present invention in Example 1 except for using the combinations of a sugar compound and a protein solubilizing agent shown below in the first reagent. The correlation of the results obtained for 20 serum with those obtained by the agarose electrophoretic method was expressed in terms of coefficient of correlation.

Composition of the First Reagent:

| | | |
|---|---|---|
| A. | Trimethyl-β-cyclodextrin | 5 mM |
| | Polyoxyethylene monolaurate | 5 g/l |
| | EMSE | 1.1 mM |
| | Tris buffer (pH 7.0) | 30 mM |
| B. | Trimethyl-β-cyclodextrin | 5 mM |
| | Sodium dodecylbenezenesulfonate | 5 g/l |
| | EMSE | 1.1 mM |
| | Tris buffer (pH 7.0) | 30 mM |
| C. | Dimethyl-β-cyclodextrin | 5 mM |
| | Polyoxyethylene monolaurate | 5 g/l |
| | EMSE | 1.1 mM |
| | Tris buffer (pH 7.0) | 30 mM |
| D. | Dimethyl-β-cyclodextrin | 5 mM |
| | Sodium dodecylbenzenesulfonate | 5 g/l |
| | EMSE | 1.1 mM |
| | Tris buffer (pH 7.0) | 30 mM |

In this method, measurements were made by using an autoanalyzer (Hitachi 7070) under the following conditions.

Sample: 4 μl

First reagent: 300 μl

Second reagent: 100 μl

Measurement wavelength:
 Main wavelength: 600 nm
 Sub-wavelength: 700 nm

The results are shown in Table 4.

TABLE 4

| First reagent | Coefficient of correlation |
|---|---|
| A | 0.9324 |
| B | 0.8227 |

TABLE 4-continued

| First reagent | Coefficient of correlation |
|---|---|
| C | 0.8523 |
| D | 0.7876 |

As shown in Table 4, the results obtained by the method of the present invention closely correlated with the results obtained by the electrophoretic method.

EXAMPLE 3

Determination of LDL cholesterol was carried out by the same procedure as in Example 2 except for using additionally a metal salt in the compositions of B and D. The correlation of the results obtained for 20 serum samples with those obtained by the agarose electrophoretic method was expressed in terms of coefficient of correlation.

Composition of the First Reagent:

| | | |
|---|---|---|
| E. | Trimethyl-β-cyclodextrin | 5 mM |
| | Sodium dodecylbenzenesulfonate | 5 g/l |
| | Mg chloride hexahydrate | 6 mg/ml |
| | EMSE | 1.1 mM |
| | Tris buffer (pH 7.0) | 30 mM |
| F. | Dimethyl-β-cyclodextrin | 5 mM |
| | Sodium dodecylbenzenesulfonate | 5 g/l |
| | Mg chloride hexahydrate | 6 mg/ml |
| | EMSE | 1.1 mM |
| | Tris buffer (pH 7.0) | 30 mM |

The results are shown in Table 5.

TABLE 5

| First reagent | Coefficient of correlation |
|---|---|
| E | 0.9302 |
| F | 0.9298 |

As shown in Table 5, the results obtained by the method of the present invention closely correlated with the results obtained by the electrophoretic method.

EXAMPLE 4

Determination of VLDL cholesterol was carried out by the method of the present invention in which the amount of VLDL cholesterol was directly determined and by the agarose electrophoretic method [Clinical Test (Rinsho Kensa), 29, 1344 (1985)] according to the same procedures as in Example 1 for comparison.

Composition of Reagents in the Method of the Present Invention:

| | |
|---|---|
| First reagent | |
| 2-Hydroxypropyl-β-cyclodextrin | 5 mM |
| Polyoxyethylene lauryl ether | 5 g/l |
| EMSE | 1.1 mM |
| Tris buffer (pH 7.0) | 30 mM |
| Second reagent | |
| Modified Cholesterol esterase | 1.0 U/ml |
| Modified Cholesterol oxidase | 5.0 U/ml |
| Peroxidase | 25 U/ml |

-continued

| | |
|---|---|
| 4-Aminoantipyrine | 2.2 mM |
| Tris buffer (pH 7.0) | 30 mM |

Modification of the enzymes was carried out in the following manner. Cholesterol esterase or cholesterol oxidase was dissolved in a 20 mM phosphate buffer (pH 8) (10 mg/ml), followed by cooling to 5° C. To the solution was added Sunbright 4001 (NOF Corporation) (20 times molar quantity of the enzyme) followed by dissolution, and the mixture was subjected to reaction at 5° C. for 4 hours to modify the enzyme with polyethylene glycol. The resulting reaction mixture was used as the modified cholesterol esterase or modified cholesterol oxidase (molecular weight of polyethylene glycol moiety=6000).

The results are shown in Table 6.

TABLE 6

| | Concentration of VLDL cholesterol (mg/dl) | |
|---|---|---|
| Sample | Method of the present invention | Electrophoretic method |
| 1 | 24 | 19 |
| 2 | 29 | 22 |
| 3 | 17 | 15 |
| 4 | 19 | 23 |
| 5 | 12 | 15 |
| 6 | 25 | 23 |
| 7 | 46 | 49 |
| 8 | 44 | 39 |
| 9 | 33 | 27 |
| 10 | 31 | 34 |

As shown in Table 6, the results obtained by the method of the present invention closely correlated with the results obtained by the electrophoretic method.

Industrial applicability

The present invention provides a simple method for the determination of LDL cholesterol or VLDL cholesterol which does not require complicated fractionation and separation steps and which is applicable to the analysis with an automatic analyzer.

We claim:

1. A method for determination of cholesterol in low-density lipoprotein (LDL) or very low-density lipoprotein (VLDL) in a sample, which comprises the steps of:
   selecting a sugar compound and a protein solubilizing agent;
   contacting a sample containing LDL or VLD with the sugar compound, the protein solubilizing agent and a reagent system for the determination of cholesterol in order to generate a product;
   determining an amount of the product; and
   correlating the amount of the product with the amount of cholesterol in LDL or VLDL in the sample.

2. A method for determination of cholesterol in low-density lipoprotein (LDL) in a sample, which comprises the steps of:
   selecting a sugar compound and a protein solubilizing agent;
   contacting a sample containing LDL with the sugar compound, the protein solubilizing agent and a reagent system for the determination of cholesterol in order to generate a product;
   determining an amount of the product; and
   correlating the amount of the product with the amount of cholesterol in LDL in the sample.

3. A method for determination of cholesterol in very low-density lipoprotein (VLDL) in a sample, which comprises the steps of:
   selecting a sugar compound and a protein solubilizing agent;
   contacting a sample containing VLDL with the sugar compound, the protein solubilizing agent and a reagent system for the determination of cholesterol in order to generate a product;
   determining an amount of the product; and
   correlating the amount of the product with the amount of cholesterol in VLDL in the sample.

4. The method according to any of claims 1–3, wherein the sugar compound is a glucose derivative.

5. The method according to claim 4, wherein the sugar compound is a compound represented by general formula (I):

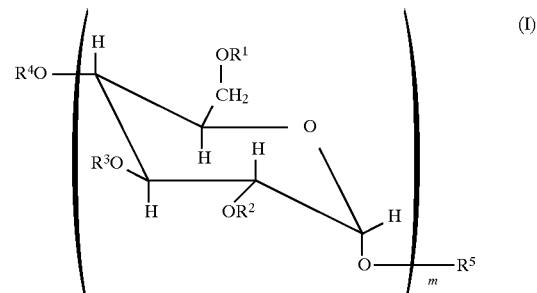

wherein $R^1$, $R^2$, and $R^3$ independently represent hydrogen, substituted or unsubstituted alkyl, substituted or unsubstituted alkanoyl, $SO_3M^2$ (in which $M^2$ is hydrogen or a metal), -(glucosyl)$_p$—H (in which p is 1 or 2), or -(maltosyl)$_q$—H (in which q is 1 or 2); $R^4$ and $R^5$ independently represent hydrogen, a metal, or $SO_3M^3$ (in which $M^3$ is hydrogen or a metal); and m is an integer of 6 to 8;

or a compound represented by general formula (II):

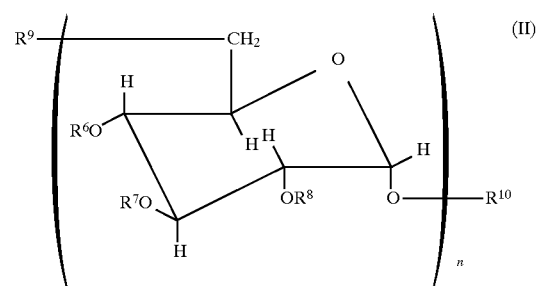

wherein $R^6$, $R^7$, and $R^8$ independently represent hydrogen or $SO_3M^4$ (in which $M^4$ is hydrogen or a metal); $R^9$ represents hydrogen, $OM^5$ (in which $M^5$ is hydrogen or a metal), or $OSO_3M^6$ (in which $M^6$ is hydrogen or a metal); $R^{10}$ represents hydrogen, a metal, or $SO_3M^7$ (in which $M^7$ is hydrogen or a metal); and n is an integer of 4 to 8000.

6. The method according to claim 5, wherein the sugar compound is a cyclodextrin derivative.

7. The method according to any of claims 1–3, wherein the protein solubilizing agent is a compound represented by general formula (III):

$$R^{11}(C_2H_4O)_a—(C_3H_6O)_bR^{12} \qquad (III)$$

wherein a and b independently represent an integer of 0 to 200; $R^{11}$ represents $R^{20}$—X—O— (in which $R^{20}$ is alkyl or alkenyl, and X is a single bond or CO) or H—$(CH_2CH_2O)_c$—$N(R^{21})$— (in which c is an integer of 1 to 200, and $R^{21}$ is alkyl or alkenyl); and $R^{12}$ represents $C_2H_4COOR^{22}$, $C_3H_6COOR^{23}$, $C_2H_4CH(COOR^{24})_2$, or $C_2H_4CH(COOR^{25})(COOR^2)$ (in which $R^{22}$, $R_{23}$, $R^{24}$, $R^{25}$, and $R^{26}$ independently represent hydrogen, a metal, alkyl, or alkenyl), provided that at least one of a and b is not 0, and —$(C_2H_4O)$— and —$(C_3H_6O)$— may be located at random;

a compound represented by general

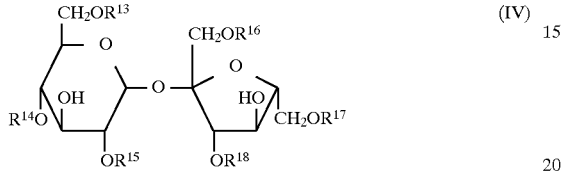

wherein $R^{13}$, $R^{14}$, $R^{15}$, $R^{16}$, $R^{17}$, and $R^{18}$ independently represent alkanoyl;

or a compound represented by general formula (V):

wherein $R^{19}$ represent alkyl, alkenyl, or substituted or unsubstituted aryl; Y represents a single bond,

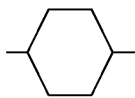

—O—, —$CH(R^{27})$— (in which $R^{27}$ is alkyl or alkenyl), —$CH_2CH(OH)(CH_2)_d$—(in which d is an integer of 1 to 22), —CH=$CH(CH_2)_e$— (in which e is an integer of 1 to 22), —$OCOCH(CH_2COOR^{28})$— (in which $R^{28}$ is alkyl or alkenyl), or a mixture thereof; and $M^1$ represents hydrogen or a metal.

8. The method according to claim 7, wherein the protein solubilizing agent is a nonionic surfactant or an anionic surfactant.

9. The method according to any of claims 1–3, wherein the determination of the amount of cholesterol is carried out in the presence of a divalent metal salt.

10. The method according to any of claims 1–3, wherein the reagent system for determination of cholesterol comprises one of the following groups (a), (b) or (c):

(a) chemically modified or unmodified cholesterol esterase, chemically modified or unmodified cholesterol oxidase, and a chromogen;

(b) chemically modified or unmodified cholesterol esterase, chemically modified or unmodified cholesterol dehydrogenase, and a reduced type coenzyme; or (c) chemically modified or unmodified cholesterol esterase, chemically modified or unmodified cholesterol dehydrogenase, a reduced type coenzyme and a chromogen.

11. A reagent for the determination of cholesterol in low-density lipoprotein or very low-density lipoprotein, which contains a sugar compound, a protein solubilizing agent, and a reagent system for the determination of cholesterol.

12. A reagent for the determination of cholesterol in low-density lipoprotein, which contains a sugar compound, a protein solubilizing agent, and a reagent system for the determination of cholesterol.

13. A reagent for the determination of cholesterol in very low-density lipoprotein, which contains a sugar compound, a protein solubilizing agent, and a reagent system for the determination of cholesterol.

14. The reagent according to any of claims 11–13, wherein the sugar compound is a glucose derivative.

15. The reagent according to claim 14, wherein the sugar compound is a compound represented by general formula (I):

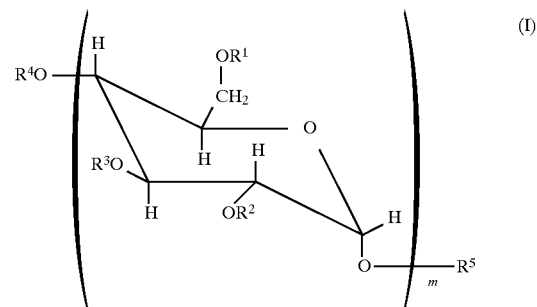

wherein $R^1$, $R^2$, and $R^3$ independently represent hydrogen, substituted or unsubstituted alkyl, substituted or unsubstituted alkanoyl, $SO_3M^2$ (in which $M^2$ is hydrogen or a metal), -(glucosyl)$_p$—H (in which p is 1 or 2), or -(meltosyl)$_q$—H (in which q is 1 or 2); $R^4$ and $R^5$ independently represent hydrogen, a metal, or $SO_3M^3$ (in which $M^3$ is hydrogen or a metal); and m is an integer or 6 to 8;

or a compound represented by general formula (II):

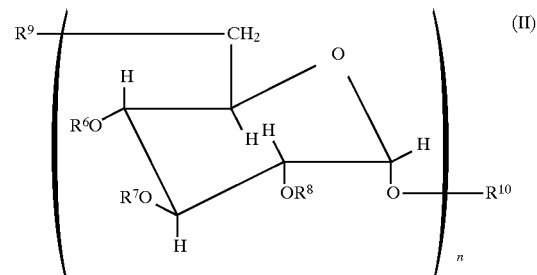

wherein $R^6$, $R^7$, and $R^8$ independently represent hydrogen or $SO_3M^4$ (in which $M^4$ is hydrogen or a metal); $R^9$ represents hydrogen, $OM^5$ (in which $M^5$ is hydrogen or a metal), or $OSO_3M^6$ (in which $M^6$ is hydrogen or a metal); $R^{10}$ represents hydrogen, a metal, or $SO_3M^7$ (in which $M^7$ is hydrogen or a metal); and n is an integer of 4 to 8000.

16. The reagent according to claim 15, wherein the sugar compound is a cyclodextrin derivative.

17. The reagent according to any of claims 11–13, wherein the protein solubilizing agent is a compound represented by general formula (III):

wherein a and b independently represent an integer of 0 to 200; $R^{11}$ represents $R^{20}$—X—O— (in which $R^{20}$ is alkyl or alkenyl, and X is a single bond or CO) or H—$(CH_2CH_2O)_c$—$N(R^{21})$— (in which c is an integer of 1 to 200, and $R^{21}$ is alkyl or alkenyl); and $R^{12}$ represents $C_2H_4COOR^{22}$, $C_3H_6COOR^{23}$, $C_2H_4CH(COOR^{24})_2$, or $C_2H_4CH(COOR^{25})(COOR^{26})$ (in which $R^{22}$, $R^{23}$, $R^{24}$, $R^{25}$, and $R^{26}$ independently represent hydrogen, a metal, alkyl, or alkenyl), provided that at least one of a and b is not 0, and —$(C_2H_4O)$— and —$(C_3H_6O)$— may be located at random;

a compound represented by general formula (IV):

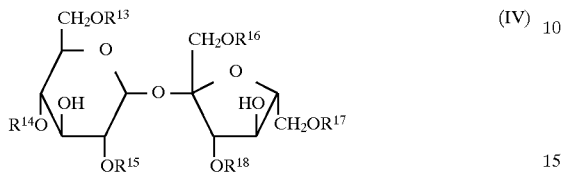
(IV)

wherein $R^{13}$, $R^{14}$, $R^{15}$, $R^{16}$, $R^{17}$, and $R^{18}$ independently represent alkanoyl;

or a compound represented by general formula (V):

$$R^{19}-Y-SO_3M^1 \quad (V)$$

wherein $R^{19}$ represents alkyl, alkenyl, or substituted or unsubstituted aryl; Y represents a single bond,

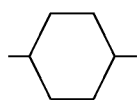

—O—, —CH($R^{27}$)— (in which $R^{27}$ is alkyl or alkenyl), —CH$_2$CH(OH) (CH$_2$)$_d$— (in which d is an integer of 1 to 22), —CH=CH(CH$_2$)$_e$— (in which e is an integer of 1 to 22), —OCOCH(CH$_2$COOR$^{28}$)— (in which $R^{28}$ is alkyl or alkenyl), or a mixture thereof; and $M^1$ represents hydrogen or a metal.

18. The reagent according to claim 17, wherein the protein solubilizing agent is a nonionic surfactant or an anionic surfactant.

19. A kit for the determination of cholesterol in low-density lipoprotein or very low-density lipoprotein comprising a first reagent containing a sugar compound and a second reagent containing a protein solubilizing agent, wherein a reagent system for the determination of cholesterol is contained in either the first reagent or the second reagent.

20. A kit for the determination of cholesterol in low-density lipoprotein comprising a first reagent containing a sugar compound and a second reagent containing a protein solubilizing agent, wherein a reagent system for the determination of cholesterol is contained in either the first reagent or the second reagent.

21. A kit for the determination of cholesterol in very low-density lipoprotein comprising a first reagent containing a sugar compound and a second reagent containing a protein solubilizing agent, wherein a reagent system for the determination of cholesterol is contained in either the first reagent or the second reagent.

22. The kit according to any of claims 19–21, wherein the sugar compound is a glucose derivative.

23. The kit according to claim 22, wherein the sugar compound is a compound represented by general formula (I):

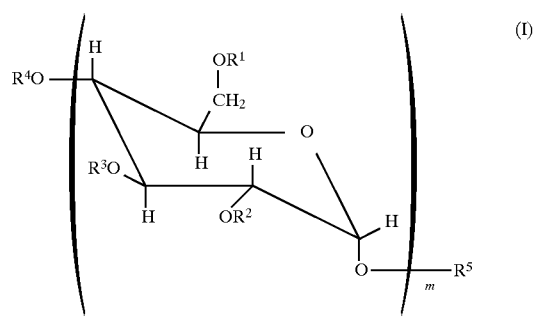
(I)

wherein $R^1$, $R^2$, and $R^3$ independently represent hydrogen, substituted or unsubstituted alkyl, substituted or unsubstituted alkanoyl, $SO_3M^2$ (in which $M^2$ is hydrogen or a metal), -(glucosyl)$_p$—H (in which p is 1 or 2), or -(maltosyl)$_q$—H (in which q is 1 or 2); $R^4$ and $R^5$ independently represent hydrogen, a metal, or $SO_3M^3$ (in which $M^3$ is hydrogen or a metal); and m is an integer of 6 to 8;

or a compound represented by general formula (II):

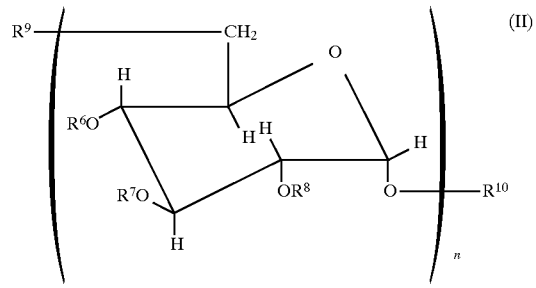
(II)

wherein $R^6$, $R^7$, and $R^8$ independently represent hydrogen or $SO_3M^4$ (in which $M^4$ is hydrogen or a metal); $R^9$ represents hydrogen, $OM^5$ (in which $M_5$ is hydrogen or a metal), or $SO_3M^6$ (in which $M^6$ is hydrogen or a metal); $R^{10}$ represents hydrogen, a metal, or $SO_3M^7$ (in which $M^7$ is hydrogen or a metal); and n is an integer of 4 to 8000.

24. The kit according to claim 23, wherein the sugar compound is a cyclodextrin derivative.

25. The kit according to any of claims 19–21, wherein the protein solubilizing agent is a compound represented by general formula (III):

$$R^{11}(C_2H_4O)_a-(C_3H_6O)_bR^{12} \quad (III)$$

wherein a and b independently represent an integer of 0 to 200; $R^{11}$ represents $R^{20}$—X—O— (in which $R^{20}$ is alkyl or alkenyl, and X is a single bond or CO) or H—(CH$_2$CH$_2$O)$_c$—N($R^{21}$)— (in which c is an integer of 1 to 200, and $R^{21}$ is alkyl or alkenyl); and $R^{12}$ represents $C_2H_4COOR^{22}$, $C_3H_6COOR^{23}$, $C_2H_4CH(COOR^{24})_2$, or $C_2H_4CH(COOR^{25})(COOR^{26})$ (in which $R^{22}$, $R^{23}$, $R^{24}$, $R^{25}$, and $R^{26}$ independently represent hydrogen, a metal, alkyl, or alkenyl), provided that at least one of a and b is not 0, and —$(C_2H_4O)$— and —$(C_3H_6O)$— may be located at random;

a compound represented by general formula (IV):

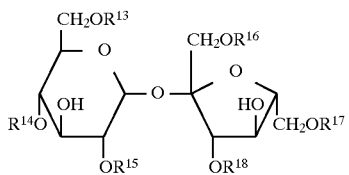 (IV)

wherein $R^{13}, R^{14}, R^{15}, R^{16}, R^{17}$, and $R^{18}$ independently represent alkanoyl; or a compound represented by general formula (V):

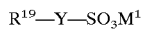 (V)

wherein $R^{19}$ represents alkyl, alkenyl, or substituted or unsubstituted aryl; Y represents a single bond,

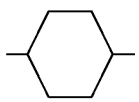

—O—, —CH($R^{27}$)— (in which $R^{27}$ is alkyl or alkenyl), —CH$_2$CH(OH)(CH$_2$)$_d$— (in which d is an integer of 1 to 22), —CH=CH(CH$_2$)$_e$— (in which e is an integer of 1 to 22), —OCOCH(CH$_2$COOR$^{28}$)— (in which $R_{28}$ is alkyl or alkenyl), or a mixture thereof; and $M^1$ represents hydrogen or a metal.

26. The kit according to claim 25, wherein the protein solubilizing agent is a nonionic surfactant or an anionic surfactant.

27. A kit for the determination of cholesterol in low-density lipoprotein or very low-density lipoprotein comprising a first reagent containing a reagent system for the determination of cholesterol and a second reagent containing a sugar compound and a protein solubilizing agent.

28. A kit for the determination of cholesterol in low-density lipoprotein or very low-density lipoprotein comprising:

a first reagent containing a sugar compound and a reagent system for the determination of cholesterol; and a second reagent containing a protein solubilizing agent, said second reagent optionally containing a sugar compound.

29. A kit for the determination of cholesterol in low-density lipoprotein or very low-density lipoprotein comprising:

a first reagent containing a portion of a reagent system for the determination of cholesterol and a sugar compound; and a second reagent containing a remaining portion of the reagent system for the determination of cholesterol and a protein solubilizing agent, said second reagent optionally containing a sugar compound.

* * * * *

UNITED STATES PATENT AND TRADEMARK OFFICE
CERTIFICATE OF CORRECTION

PATENT NO.    : 5,888,827
DATED         : March 30, 1999
INVENTOR(S)   : NORIHIKO KAYAHARA, ET AL.

It is certified that error appears in the above-identified patent and that said Letters Patent is hereby corrected as shown below:

AT [57] ABSTRACT

Line 2, "(VLVL)" should read --(VLDL)--.

COLUMN 4

Line 14, "presence." should read --presence--; and
   Line 24, "enxyme" should read --enzyme--.

COLUMN 6

Line 48, "cholesterol" (second occurrence) should read --cholesterol,--.

COLUMN 9

Line 30, "serum" should read --serum samples--.

COLUMN 11

Line 51, "VLD" should read --VLDL--.

UNITED STATES PATENT AND TRADEMARK OFFICE
CERTIFICATE OF CORRECTION

PATENT NO.  : 5,888,827
DATED       : March 30, 1999
INVENTOR(S) : NORIHIKO KAYAHARA, ET AL.                  Page 2 of 3

It is certified that error appears in the above-identified patent and that said Letters Patent is hereby corrected as shown below:

COLUMN 13

Line 8, "$R_{23}$," should read --$R^{23}$,--; and
  Line 12, "general" should read
--general formula (IV):--.

COLUMN 14

Line 31, "-(meltosyl)$_q$-H" should read
-- -(maltosyl)$_q$-H--.

COLUMN 15

Line 34, "-CH=CH(CH$_2$)$_c$-" should read -- -CH=CH(CH$_2$)$_e$- --.

UNITED STATES PATENT AND TRADEMARK OFFICE
CERTIFICATE OF CORRECTION

PATENT NO. : 5,888,827
DATED : March 30, 1999
INVENTOR(S) : NORIHIKO KAYAHARA, ET AL.

It is certified that error appears in the above-identified patent and that said Letters Patent is hereby corrected as shown below:

COLUMN 17

Line 27, "$-CH=CH(CH_2)_c-$" should read -- $-CH=CH(CH_2)_e-$ --; and

Line 29, "$R_{28}$" should read -- $R^{28}$ --.

Signed and Sealed this

Fourteenth Day of December, 1999

Q. TODD DICKINSON

*Attesting Officer*   Acting Commissioner of Patents and Trademarks